(12) United States Patent
Russo

(10) Patent No.: US 6,419,660 B1
(45) Date of Patent: Jul. 16, 2002

(54) MEDICAL TUBE HOLDER

(76) Inventor: Ronald D. Russo, 8 Candleberry Rd., Barrington, RI (US) 02806

(*) Notice: Subject to any disclaimer, the term of this patent is extended or adjusted under 35 U.S.C. 154(b) by 0 days.

(21) Appl. No.: 09/233,414

(22) Filed: Jan. 19, 1999

Related U.S. Application Data

(60) Provisional application No. 60/087,118, filed on May 29, 1998.

(51) Int. Cl.$^7$ .................................................. A61M 5/32
(52) U.S. Cl. ........................................ 604/180; 128/26
(58) Field of Search ................................ 604/174–180; 128/DIG. 26, DIG. 15; 602/41

(56) References Cited

U.S. PATENT DOCUMENTS

| | | | |
|---|---|---|---|
| 3,146,778 A | 9/1964 | Krawiec | 128/349 |
| 3,288,136 A | 11/1966 | Lund | 128/133 |
| 3,430,300 A | 3/1969 | Doan | 24/73 |
| 3,826,254 A | 7/1974 | Mellor | 128/133 |
| 3,834,380 A | 9/1974 | Boyd | 128/133 |

(List continued on next page.)

FOREIGN PATENT DOCUMENTS

| | | | | |
|---|---|---|---|---|
| GB | 2235629 A | * | 3/1991 | 604/180 |
| WO | WO 99/55410 | | 4/1999 | |

OTHER PUBLICATIONS

Transatlantic, "Transafix" advertisement, Sep. 1998 (1 page).
Dale Hug Hospital Utility Grip, product sheet No. 930, Dale Medical Products, Inc., holds tubes and cords securely 1980.
Security plus Comfort, UC Strip, product information sheets, Genetic Laboratories, catheter fastener.
Immobile, product information sheets, TNT Moborg International Limited, adhesive tab for holding patient lines.
Percu–Stay, product information sheets, Genetic Laboratories, catheter and tube fastener for percutaneous drainage.
Cath–Strip, product information sheets, Genetic Laboratories, reclosable catheter fastener.
TECNOL, product information sheets, Tecnol, Inc. Secure–All™ Tube Holder, for securing any size tube or catheter.
Cath–Secure, product information sheets, M.C. Johnson Co., Inc., multi–purpose tube holder.
Immobilé™, product information sheets, TNT Moborg International Limited, secures patient lines.
Flexi–Trak™, product information sheets, E–Med Corporation, secures tubes in place.

(List continued on next page.)

*Primary Examiner*—Anhtuan T. Nguyen
*Assistant Examiner*—Michael M. Thompson
(74) *Attorney, Agent, or Firm*—Finnegan, Henderson, Farabow, Garrett & Dunner L.L.P.

(57) ABSTRACT

A tube holder and a method for manufacturing the tube holder is provided. The tube holder includes a base for attachment to a surface, for example, a patient's skin, and a tab for securing the tube to the base. According to one embodiment, the tube holder includes a first layer having first and second sides and first and second sections, and a second layer having first and second sides and first and second sections. The first sides of the first and second layers are attached to one another in the first sections of the first and second layers, the second sections of the first sides of the first and second layers are unattached to one another, and the first sections of the first and second layers form the tab and the second sections form the base. The tube holder also includes a third layer attached to the second side of the first layer for receiving a tube.

11 Claims, 6 Drawing Sheets

U.S. PATENT DOCUMENTS

| | | | |
|---|---|---|---|
| 4,074,397 A | 2/1978 | Rosin | 24/73 |
| 4,122,857 A | 10/1978 | Haerr | 128/345 |
| 4,165,748 A | 8/1979 | Johnson | 128/348 |
| 4,308,642 A | 1/1982 | Heyman | 24/306 |
| 4,324,237 A | 4/1982 | Burraravoli | 604/180 |
| 4,457,754 A | 7/1984 | Burraravoli | 128/214 |
| 4,534,762 A | 8/1985 | Heyer | 604/180 |
| 4,569,348 A | 2/1986 | Hasslinger | 604/179 |
| 4,583,976 A | 4/1986 | Ferguson | 604/174 |
| 4,639,980 A | 2/1987 | Peterson | 24/306 |
| 4,662,366 A | 5/1987 | Tari | 128/134 |
| 4,671,787 A | 6/1987 | Widman | 604/179 |
| 4,702,736 A | 10/1987 | Kalt et al. | 604/180 |
| 4,706,914 A | 11/1987 | Ground | 248/74.3 |
| 4,726,716 A | 2/1988 | McGuire | 604/174 |
| 4,737,143 A | 4/1988 | Russell | 604/180 |
| 4,738,662 A | 4/1988 | Kalt et al. | 604/180 |
| 4,822,342 A | 4/1989 | Brawner | 604/180 |
| 4,838,878 A | 6/1989 | Kalt et al. | 604/180 |
| 4,976,700 A | 12/1990 | Tollini | 604/180 |
| 4,988,338 A | 1/1991 | Taylor et al. | 604/180 |
| 5,037,397 A | 8/1991 | Kalt et al. | 604/174 |
| 5,098,399 A * | 3/1992 | Tollini | |
| 5,100,393 A | 3/1992 | Johnson | 604/180 |
| 5,147,322 A | 9/1992 | Bowen et al. | 604/180 |
| 5,167,050 A | 12/1992 | Korsen | 24/16 R |
| 5,200,245 A | 4/1993 | Broderick, Jr. | 428/100 |
| 5,304,146 A | 4/1994 | Johnson et al. | 604/180 |
| 5,308,339 A * | 5/1994 | Kalt et al. | 604/180 |
| 5,397,639 A * | 3/1995 | Tollini | 604/180 |
| 5,451,725 A | 9/1995 | Goldman | 181/131 |
| 5,468,231 A * | 11/1995 | Newman et al. | 604/180 |
| 5,709,665 A | 1/1998 | Vergano et al. | 604/174 |
| 5,785,690 A * | 7/1998 | Newman et al. | 604/180 |
| 5,797,884 A * | 8/1998 | Byrd | 604/180 |
| 6,015,119 A | 1/2000 | Starchevich | 248/65 |

OTHER PUBLICATIONS

Ansley, product information sheets, Ansley, a division of Struckmeyer, tube holders.

Zefon Medical Products, product information sheets, Dale Medical Products tube, catheter and line attachment.

Cath–Control, product information sheet, Anago, catheter anchor.

Inside Advantage, Cath–Control™, product information sheets, Advantabe Medical, catheter tube holder.

Cath–Secure, product information sheets, M.C. Johnson Co., Inc., secures catheter.

Cath–Secure Dual Tab™, product information sheets, M.C. Johnson Co., Inc., new multi–purpose medical tube holder.

Catheter Fastener, product information sheets, Genetic Laboratories one piece design, urinary catheter fastener.

Tube Strip, product information sheet, E–I–MED Corporation, multipurpose tubing and monitor line securement strips.

* cited by examiner

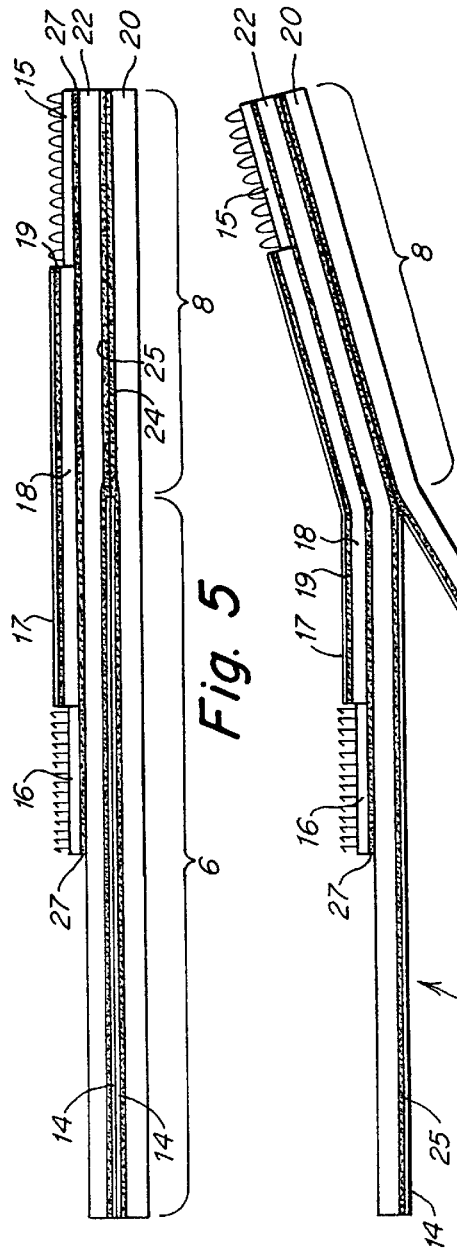
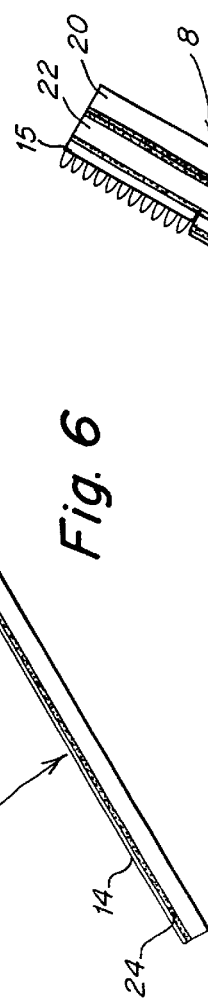
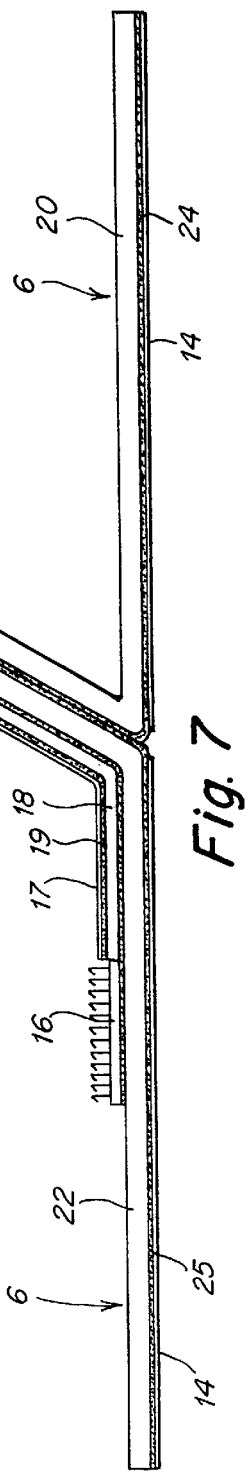

MEDICAL TUBE HOLDER

CROSS REFERENCE TO RELATED APPLICATIONS

This application claims priority to provisional application Ser. No. 60/087,118, filed May 29, 1998, entitled ALL PURPOSE TUBE HOLDER, which prior application is incorporated herein by reference.

FIELD OF INVENTION

The present invention relates to a tube holder, which can be used, for example, in medical applications. The present invention further relates to a method of manufacturing the tube holder.

BACKGROUND OF INVENTION

Various medical devices are used in close proximity to a patient. Certain devices, for example, infusion and drainage tubes, are secured directly onto the patient to avoid having the tube interfere with the patient's movement, or the movement of a care giver when working on the patient. Movement, advancement or retraction of such tubes is frequently necessary.

Medical tape or bandages are typical fasteners used to attach such devices to the patient. These fasteners may not necessarily ensure that the medical device is reliably secured onto the patient. Furthermore, when using medical tape, if it is necessary to move, advance or retract the tube, as is often the case, the medical tape is ripped off the patient's skin, causing discomfort and irritation.

Accordingly, it is an object of the present invention to provide an improved, easy to manufacture, tube holder.

SUMMARY OF THE INVENTION

A tube holder and a method for manufacturing the tube holder is provided. The tube holder includes a base for attachment to a surface, for example, a patient's skin, and a tab for securing the tube to the base.

In one embodiment, the tube holder includes a base and a tab extending therefrom. The tube holder also includes a first layer having first and second sides and first and second sections, and a second layer having first and second sides and first and second sections. The first sides of the first and second layers are attached to one another in the first sections of the first and second layers, the second sections of the first sides of the first and second layers are unattached to one another, and the first sections of the first and second layers form the tab and the second sections form the base. The tube holder also includes a third layer attached to the second side of the first layer for receiving a tube.

According to another embodiment, the tube holder includes a base and a tab extending from the base, the tab having first and second sides. The base is for attachment to a patient adjacent the first and second sides of the tab, and the first side of the tab is for attachment to the base to secure a tube between the tab and base. The tube holder also includes a layer for receiving the tube, the layer attached to and overlapping both the first side of the tab and the base.

According to another embodiment, a method of manufacturing a tube holder is provided that includes the steps of forming a first layer having partially exposed and partially covered adhesive thereon and forming a second layer on top of said first layer. The second layer has partially exposed and partially covered adhesive thereon and is oriented so that the exposed adhesive on the first layer adheres to the exposed adhesive on the second layer and the covered adhesive on the second layer faces the covered adhesive on the first layer. The method also includes forming a third layer on top of said second layer for receiving said tubing.

BRIEF DESCRIPTION OF THE DRAWINGS

The invention will be better understood and appreciated from the following detailed description of illustrative embodiments thereof, and the accompanying drawings, in which:

FIG. 5 illustrates a somewhat schematic end view of the completed tube holder of FIG. 1 after the manufacturing process, in a closed state;

FIG. 6 illustrates a somewhat schematic end view of the completed tube holder of FIG. 1 with the tube holder in a semi-opened state;

FIG. 7 illustrates a somewhat schematic end view of the completed tube holder of FIG. 1 with the tube holder in an open, ready-to-use state;

DETAILED DESCRIPTION

The present invention relates to a tube holder and methods for making the tube holder.

Figure 1:
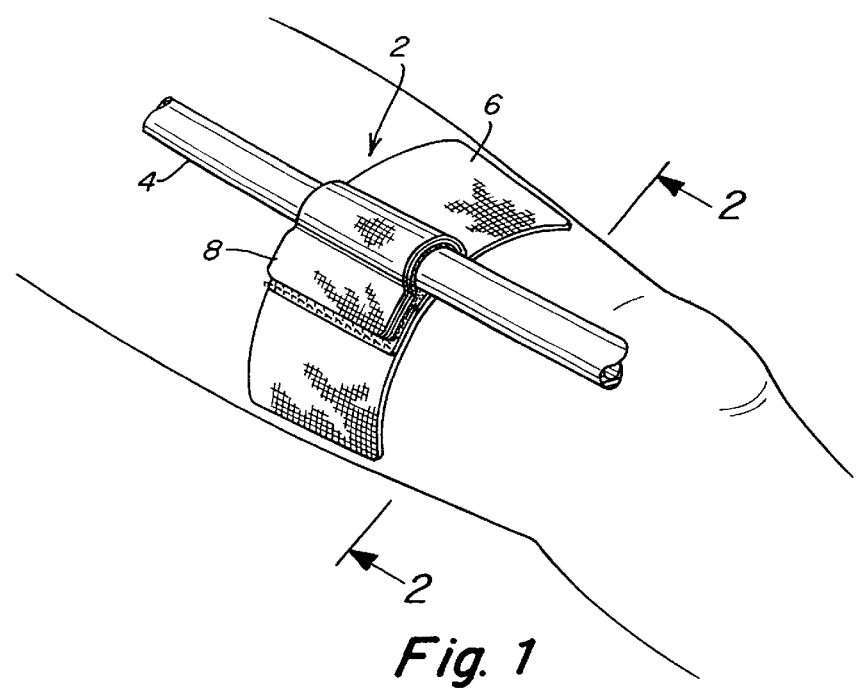
FIG. 1 illustrates a perspective view a tube holder according to one embodiment secured to a patient's leg.
Figure 2:
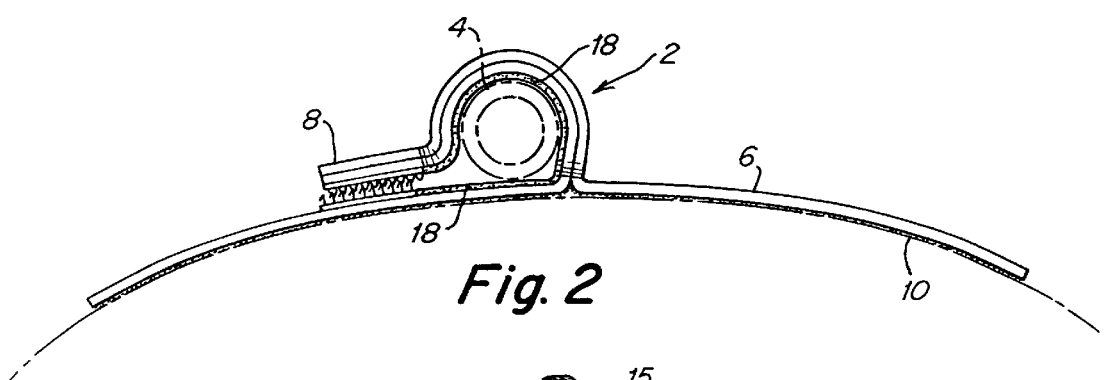
FIG. 2 illustrates an end view of the tube holder of FIG. 1 along line 2—2.
Figure 3:
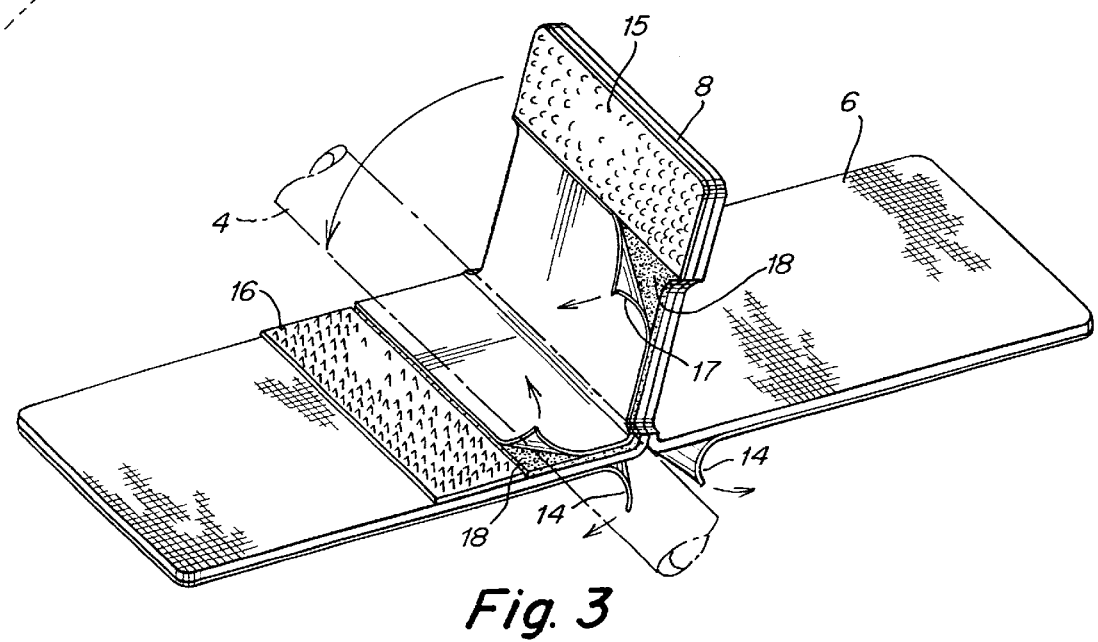
FIG. 3 illustrates an enlarged version of the tube holder of FIG. 1, in the open position prior to use.

FIGS. 1–3 illustrate a tube holder 2 according to one embodiment of the invention. The tube holder shown herein can be used in medical applications in which a tube, for example, an infusion, drainage or catheter tube, is secured to a patient's skin.

The tube holder 2 is shown in FIGS. 1–2 securing a tube 4 to a patient's leg. Tube holder 2 includes a base 6 and a tab 8. The base 6 is adhered to the patient and the tab 8 is folded over the tube and secured to a section of the base—thereby securing the tube in place. To adhere the tube holder 2 to the patient, the base 6 includes an adhesive 10 thereon disposed beneath release liners 14 (see FIGS. 2 and 3). When the release liners are peeled off, adhesive 10 is exposed so that the base can be attached to the patient's skin, or other surface.

The tab 8 includes loops 15 attached thereto adapted to mate with hooks 16 attached to the base to secure the tube in place. Alternatively, the hook portion can be formed on the tab and the loop portion can be formed on the base, or another appropriate fastener can be used. Velcro® is an example of loop and hook fastener that can be used.

A layer 18 is attached to both base 6 and tab 8. The layer is disposed on the portions of the tab and base that receive the tube 4. The layer 18 includes adhesive thereon for engaging and securing the tube 4. Release liner 17 is disposed over the layer 18 and is removed prior to securing the tube. The layer 18 encircles and conforms to the shape of the tube and provides an inward surrounding compressive force on the tube to enhance the gripping power of the adhesive disposed on the layer. The layer is, for example, polyethylene foam. The adhesive on the layer 18 is preferably a non-permanent adhesive that permits easy attachment, removal, and reattachment of the tube 4 so the tube can be advanced or retracted. An example of an appropriate adhesive is Avery 8306 adhesive. Further, the adhesive and release liner could be applied directly to the base and tab in which case the foam layer 18 would not be used.

Figure 4:
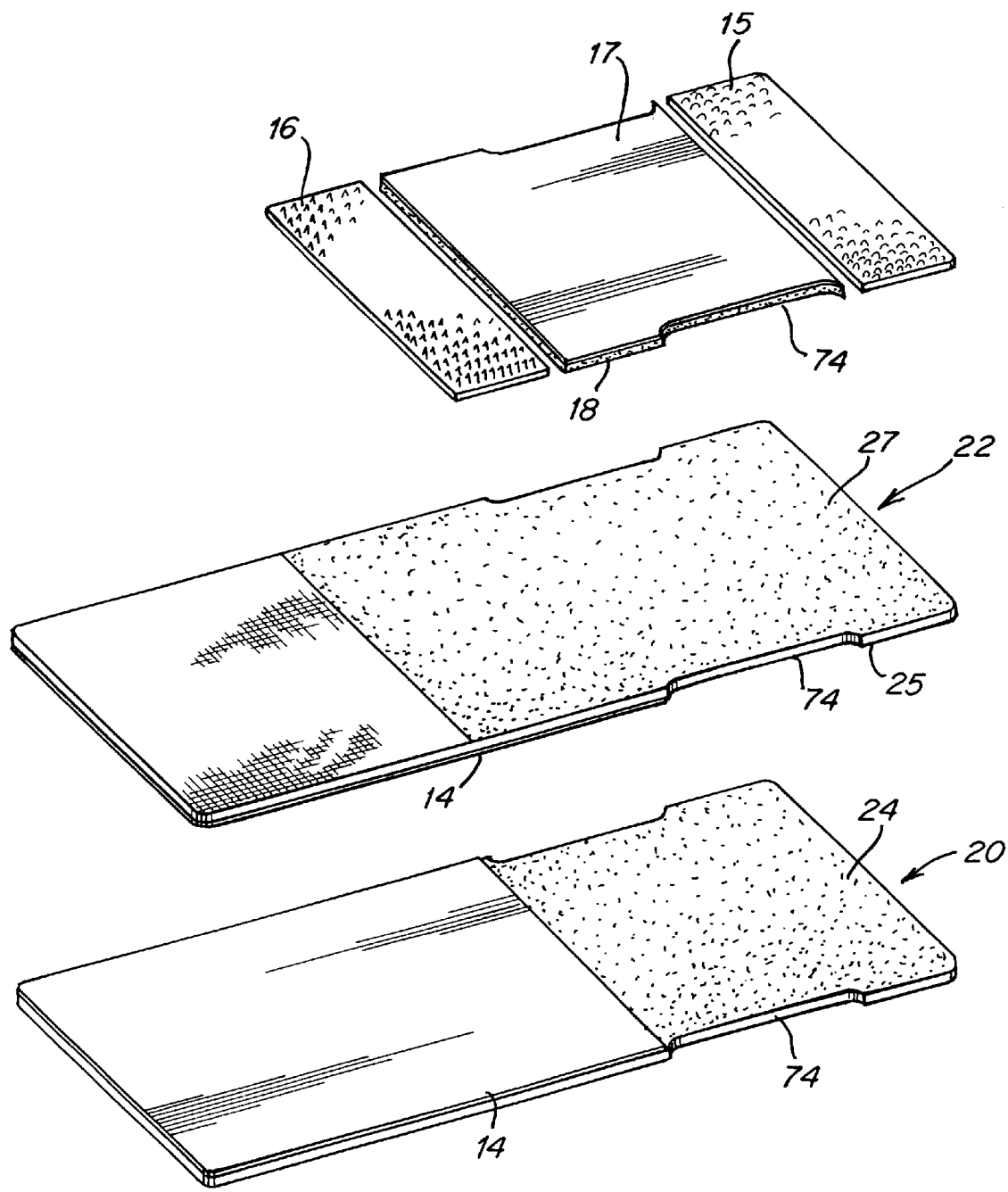
FIG. 4 illustrates an exploded perspective view of the tube holder of FIG. 1.

To form the tube holder 2 shown in FIGS. 1–3 a layered arrangement of materials is used. One embodiment of such arrangement is shown in FIGS. 4–7. FIG. 4 shows an exploded view of the tube holder, while FIGS. 5, 6 and 7 show a schematic side view of the assembled tube holder in which the various layers and adhesives have been enlarged to better show how the tube holder is arranged.

The tube holder includes a first layer 20 and a second layer 22 combined to form the base 6 and the tab 8. Preferably, a flexible, resilient, breathable material is used, especially if the tube holder is to be attached to a patient's skin. An appropriate material is, for example, Durapore®.

Layer 20 is covered with an adhesive 24 on one side thereof. One section of the adhesive 24 is exposed, while another section is covered by release liner 14. Layer 22 also includes an adhesive 25 on one side thereof, and, like layer 20, one section of adhesive 25 is exposed while another section is covered by release liner 14.

An adhesive 27 is disposed on the side of layer 22 opposite the side having adhesive 25 and release liner 14 disposed thereon. Adhesive 27 is used to attach loop layer 15, hook layer 16 and foam layer 18 to layer 22. Foam layer 18 includes a release liner 17 thereon that covers an adhesive 19 (see FIG. 5) for securing the tube.

To assemble the tube holder, layer 20 is attached to layer 22 by contacting exposed adhesive 24 of layer 20 to exposed adhesive 25 of layer 22. Release liners 14 also contact one another but the layers 20 and 22 remained unattached in the sections of the sides of these layers that include the release liners 14.

As shown in FIGS. 5, 6 and 7, the sections of the layers 20 and 22 that are covered by release liner 14 form base 6 while the sections of layers 20 and 22 that are attached by adhesives 24 and 25 form tab 8. Although fully assembled in FIG. 5, and oriented in a flat position convenient for shipping, the tube holder is not oriented for attachment. To prepare the tube holder for attachment, the sections of layers 20 and 22 covered by release liners 14 are separated from one another (FIG. 6) to form a substantially flat attachment surface (FIG. 7). FIG. 7 shows the tube holder oriented so that it can be attached to the patient, or other surface, by peeling off release liners 14. Release liner 17 is peeled off to expose adhesive 19 for receiving a tube. The tab 8 can then be folded over the tube and secured to the base by hook and loop layers 16 and 15.

The use of hook 16 and loop 15 fasteners, and a non-permanent adhesive 19, enable the tab 8 to releasably engage the tube so that the tube can be attached, removed and reattached while the tube holder remains secured to the patient.

The "layered" arrangement of the foregoing tube holder is of a construction convenient for in-line automated production. One possible embodiment of a method of manufacturing the foregoing tube holder is shown somewhat schematically in FIG. 8. The tube holder is formed by disposing layers of material upon one another to form the arrangement shown in FIG. 5.

Figure 8:
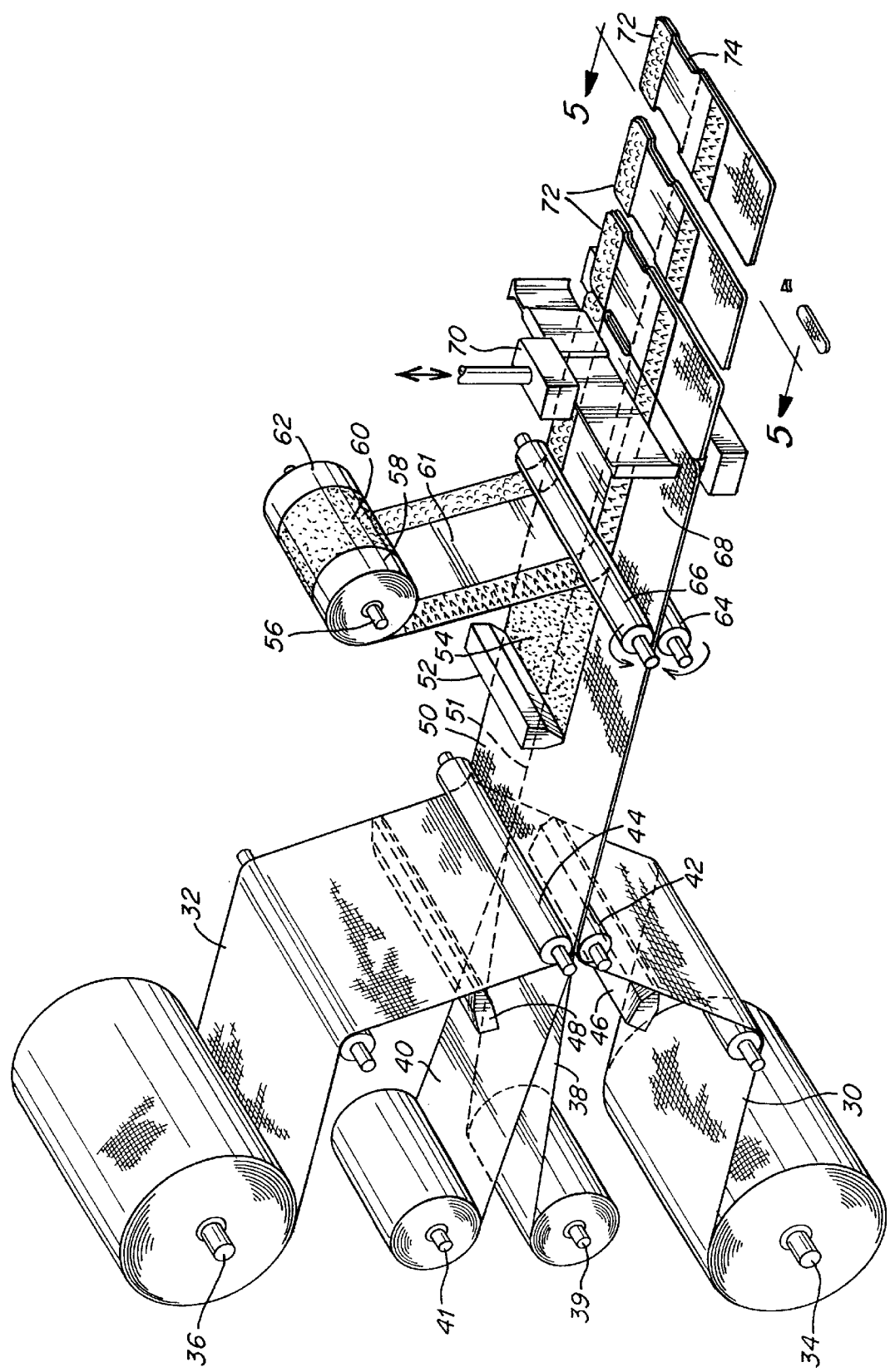
FIG. 8 illustrates a somewhat schematic perspective view of one embodiment of an automated method for manufacturing the tube holder of FIG. 1.

The automated assembly system and method shown in FIG. 8 includes sheets of material 30 and 32 fed from rollers 34 and 36 to crimp rollers 42 and 44, respectively. Material 30 and 32 forms layers 20 and 22 of the tube holder 2, respectively. Sheets of release liner 38 and 40 are fed from rollers 39 and 41 and attached to sheets of material 30 and 32 at crimp rollers 42 and 44 after adhesive is applied to material 30 and 32 from dispensers 46 and 48. Release liner 38 and 40 form release liners 14 of the tube holder. The adhesive from dispensers 46 and 48 form adhesives 24 and 25 of the tube holder. Alternatively, Durapore® material can be used in which the material 30 and 32 would already have release liner and adhesive attached.

After leaving the crimp rollers 42 and 44, the sheets of material 30 and 32 are adhered to one another in the section 50 uncovered by release liners 38 and 40. Dashed line 51 indicates the edge of the release liners and the area 50 where the materials 30 and 32 are attached. If Durapore® is used the release liners would be cut off of materials 30 and 32 to create section 50 uncovered by release liner. Another adhesive dispenser 52 applies adhesive 54 to the surface of material 32. The adhesive 54 forms adhesive 19 (see FIG. 5) of the tube holder. A roller 56 supports sheets of hook material 58, foam material 60, and loop material 62 which are fed through crimp rollers 64 and 66 and attached to material 32 via adhesive 54. Material 58 forms hooks 16 of the tube holder; material 60 forms layer 18 of the tube holder; and material 62 forms loops 15 of the tube holder. The foam material 60 includes a release liner 61 thereon and adhesive beneath the release liner that form liner 17 and adhesive 19 of the tube holder (see FIG. 5). The layers which comprise the tube holder are complete as leave the crimp rollers 64 and 66.

The completed sheet 68 of attached layers is fed to a die cutter 70 which cuts equally spaced sections of the sheet 68 to form individual tube holders 72. The die cutter can be designed to cut an indentation 74 to indicate where the tab 8 begins and the area of the tab that is to be secured to the tube.

Figure 9:
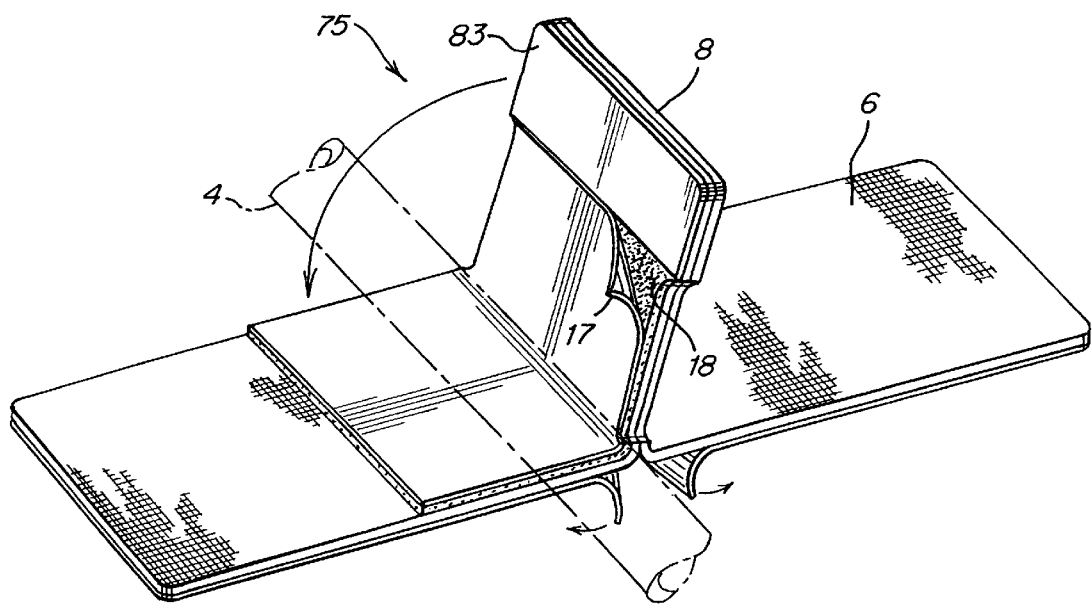
FIG. 9 illustrates a perspective view of an alternative embodiment of a tube holder, in the open position prior to use.
Figure 10:
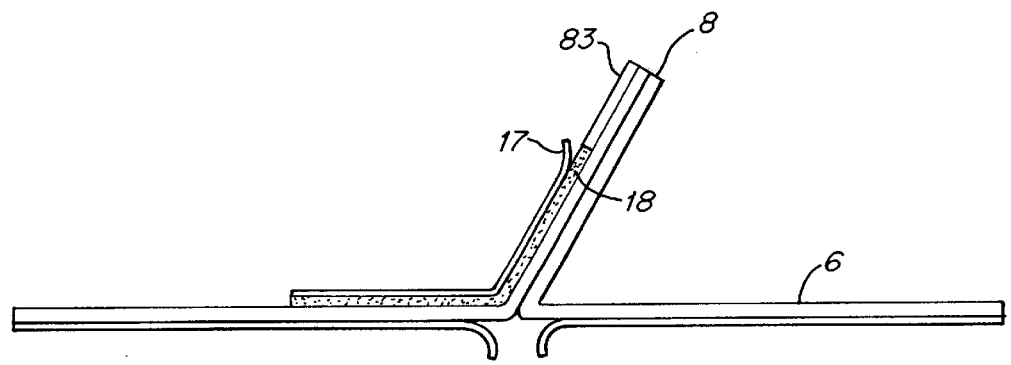
FIG. 10 illustrates a somewhat schematic end view of the tube holder of FIG. 9 prior to use.
Figure 11:
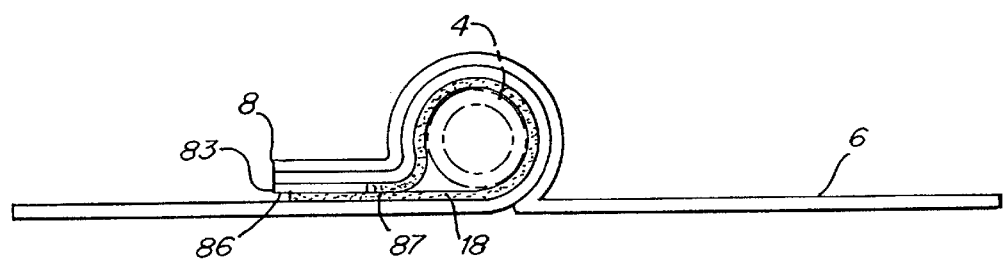
FIG. 11 illustrates a somewhat schematic end view of the tube holder of FIG. 9 in the closed position holder a tube.

FIGS. 9–11 show an alternative embodiment of a tube holder 75. The tube holder 75 is substantially the same as the tube holder described with reference to FIGS. 1–8 above, with the exception that loop and hook sections 15 and 16 have been eliminated and a non-adherent material 83 is attached to the tab to facilitate opening and closing the tab. An appropriate non-adherent material is, for example, polyester film. Alternatively, layer 18 can be used alone in which neither material 83 nor loop and hook sections 15 and 16 are used.

As shown in FIG. 11, when the tube is secured layer 18 (having adhesive thereon as described above) overlaps and attaches to itself at 87. Layer 18 is longer along tab 8 and base 6 than in FIGS. 1–8 so that the layer 18 overlaps itself. Tab 8 overhangs layer 18 at 86 to facilitate opening the tab.

Figure 12:
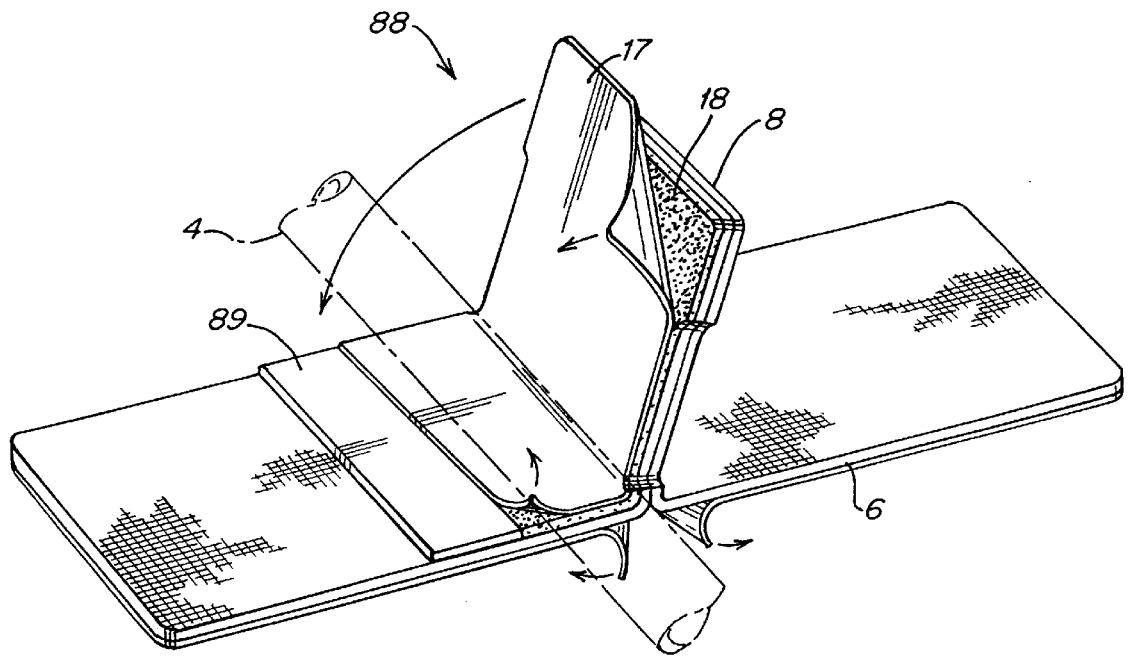
FIG. 12 illustrates a perspective view of another alternative embodiment of a tube holder, in the open position prior to use.
Figure 13:
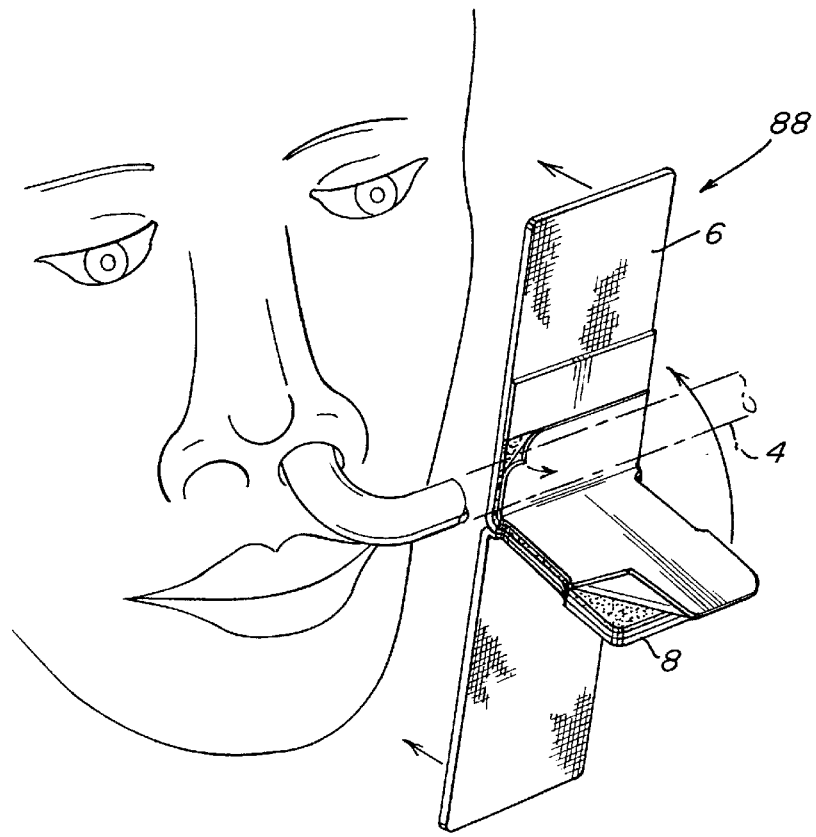
FIG. 13 illustrates one application of the tube holder of FIG. 12.

FIGS. 12 and 13 show another alternative embodiment of a tube holder 88 similar to the tube holder shown in FIGS. 9–11. In this embodiment, however, a non adherent material 89 is attached to the base to facilitate opening the tab. Also, the layer 18 completely covers the tab. The release liner 17 overhangs the end of the tab to facilitate removal of the release liner from the layer 18. FIG. 13 shows an application of the tube holder 88 in which the tube holder is used to secure a naso-gastric tube 4 to the side of a patient's cheek or forehead. The other tube holders described herein can also be used in this and other applications interchangeably.

Having thus described certain embodiments of the present invention, various alterations, modifications, and improvements will readily occur to those skilled in the art. Such alterations, modifications, and improvements are intended to be within the spirit and scope of the invention. Accordingly, the foregoing description is by way of example only, and not intended to be limiting.

What is claimed is:

1. A tube holder having a base and a tab extending therefrom comprising:

a first layer having first and second sides and first and second sections;

a second layer having first and second sides and first and second sections, wherein the first sides of the first and second layers are attached to one another in the first sections of the first and second layers, the second sections of the first sides of the first and second layers are unattached to one another, the first sections of the first and second layers form the tab and the second sections form the base, the first sides of the second sections that form the base for anchoring the tube holder to a patient's skin, and the tab for attachment to the second side of the second section of the first layer to secure a tube between the tab and the base; and a third adhesive layer attached to the second side of the first layer for receiving the tube, the adhesive layer being non-permanent to permit releasable engagement of the tube so that the tube can be removed and repositioned relative to the adhesive layer.

2. The tube holder of claim 1, wherein the third layer overlaps the tab and the base.

3. The tube holder of claim 1, further comprising a release liner disposed on said adhesive layer.

4. The tube holder of claim 1, wherein the third layer includes a foam layer having an adhesive disposed thereon.

5. The tube holder of claim 1, wherein the third layer overlaps the tab and the base.

6. The tube holder of claim 1, wherein the second sections include release liners disposed on the first sides of the first and second layers, the release liners covering adhesive disposed on, the first sides.

7. The tube holder of claim 1, further comprising means for removably attaching the tab to the base to secure the tube.

8. The tube holder of claim 7, wherein the means for removably attaching include hook and loop sections attached to the tab base, respectively, adjacent the third layer.

9. The tube holder of claim 1, wherein the first and second layers are substantially rectangular.

10. The tube holder of claim 1, wherein the first and second layers are substantially a same sizes.

11. The tube holder of claim 10, wherein the first and second layers are substantially a same sizes.

* * * * *